(12) United States Patent
Schmitt et al.

(10) Patent No.: US 9,439,606 B2
(45) Date of Patent: Sep. 13, 2016

(54) INTERVENTIONAL APPARATUS ACTIVATED COMPUTED TOMOGRAPHY (CT)

(75) Inventors: Holger Schmitt, Hamburg (DE); Michael Grass, Buchholz in der Nordheide (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 558 days.

(21) Appl. No.: 13/992,421

(22) PCT Filed: Nov. 25, 2011

(86) PCT No.: PCT/IB2011/055295
§ 371 (c)(1),
(2), (4) Date: Jun. 7, 2013

(87) PCT Pub. No.: WO2012/077011
PCT Pub. Date: Jun. 14, 2012

(65) Prior Publication Data
US 2013/0261439 A1    Oct. 3, 2013

Related U.S. Application Data

(60) Provisional application No. 61/421,303, filed on Dec. 9, 2010.

(51) Int. Cl.
*A61B 6/03* (2006.01)
*A61B 6/00* (2006.01)
(Continued)

(52) U.S. Cl.
CPC ............ *A61B 6/032* (2013.01); *A61B 5/0084* (2013.01); *A61B 5/055* (2013.01); *A61B 5/742* (2013.01); *A61B 6/037* (2013.01); *A61B 6/463* (2013.01); *A61B 6/542* (2013.01); *A61B 6/547* (2013.01); *A61B 8/0841* (2013.01); *A61B 8/463* (2013.01); *A61B 34/20* (2016.02); *A61B 90/98* (2016.02); *A61M 25/0108* (2013.01); *A61M 25/0127* (2013.01); *A61B 6/12* (2013.01); *A61B 6/4423* (2013.01); *A61B 2034/2055* (2016.02); *A61B 2034/2059* (2016.02); *A61B 2034/2065* (2016.02); *A61B 2090/3945* (2016.02); *A61M 25/0113* (2013.01); *A61M 2025/0008* (2013.01); *A61M 2025/0166* (2013.01)

(58) Field of Classification Search
None
See application file for complete search history.

(56) References Cited

U.S. PATENT DOCUMENTS 4,887,605 A * 12/1989 Angelsen ............... A61B 8/06
600/439
5,938,602 A * 8/1999 Lloyd ................. A61B 8/0833
600/424

(Continued)

FOREIGN PATENT DOCUMENTS

| JP | 2003-528687 | 9/2003 |
|----|-------------|--------|
| JP | 2008516722  | 11/2013 |
| WO | 2009083851  | 7/2009 |

*Primary Examiner* — Long V Le
*Assistant Examiner* — Bradley Impink (57) ABSTRACT

A system (100) includes an interventional apparatus (102) and an imaging scanner (101). The interventional apparatus includes a interventional instrument (204) configured to perform an image-guided interventional procedure for a patient. The interventional apparatus includes a position detector (122) that detects a position of the interventional instrument within a region of the patient at which the image-guided interventional procedure is performed from outside of the region of interest and generates a signal indicative of the detected position. The imaging scanner includes a controller (114) that activates the imaging scanner to scan the region of interest and the interventional instrument therein for one or more data acquisition cycles based on the movement signal.

20 Claims, 6 Drawing Sheets

(51) Int. Cl.
  *A61B 5/00* (2006.01)
  *A61B 5/055* (2006.01)
  *A61B 8/08* (2006.01)
  *A61B 8/00* (2006.01)
  *A61B 6/12* (2006.01)
  *A61M 25/01* (2006.01)
  *A61M 25/00* (2006.01)

(56) References Cited

U.S. PATENT DOCUMENTS 6,106,301 A * 8/2000 Merril .................. G09B 23/285
                                                    434/262
2004/0034297 A1   2/2004  Darrow et al.
2004/0147837 A1   7/2004  MaCaulay et al.
2005/0197557 A1   9/2005  Strommer et al.
2007/0103437 A1   5/2007  Rosenberg
2007/0167700 A1   7/2007  Rahn et al.
2008/0146942 A1 * 6/2008  Dala-Krishna .......... A61B 6/12
                                                    600/466
2009/0137952 A1   5/2009  Ramamurthy et al.
2009/0234220 A1 * 9/2009  Maschke ................ A61B 5/411
                                                    600/411
2011/0021926 A1 * 1/2011  Spencer ............... A61B 5/0062
                                                    600/478
2011/0319752 A1 * 12/2011 Steinberg ................ A61B 6/12
                                                    600/424

* cited by examiner

INTERVENTIONAL APPARATUS ACTIVATED COMPUTED TOMOGRAPHY (CT)

FIELD OF THE INVENTION

The following generally relates to imaging and more particular to activating an imaging scanner to scan a region of interest of a subject and an interventional instrument (of an interventional apparatus) therein based on movement of the interventional instrument within the region of interest as determined by the interventional apparatus, and is described with particular application to a computed tomography (CT) imaging scanner; however, the following is also amenable to other imaging modalities.

BACKGROUND OF THE INVENTION

Interventional imaging includes using images to guide minimally invasive interventional procedures such as diagnostic, treatment, and/or other interventional procedures.

By way of example, with one transcatheter interventional procedure, a local anesthetic is injected or applied into the skin of a patient at an entry area to numb the entry area, a puncture is made to the entry area with a needle, scalpel, etc., and a plastic sheath is inserted into the artery. A catheter supporting an interventional instrument is then inserted and feed through the sheath and into the vessel, and moved to an area of interest of the patient, such as the heart, the brain, the lungs or other anatomical structure of interest, where the interventional procedure is performed.

The interventional instrument can then be employed to perform the interventional procedure. During the interventional procedure, images are periodically acquired and used to give the interventionalist orientation and update information on the progress of the procedure. Computed tomography (CT) images have been used to guide interventional procedures. However, since CT data acquisitions can deposit a relatively high amount of x-ray radiation dose, images in CT guided interventional procedures generally are acquired very rarely and only when needed. For example, typically, an image update is only acquired after the catheter has been moved or translated, forward or backward, a certain distance, since such movement may result in a change in the interventional situation.

Unfortunately, the interventionalist performing the interventional procedure has to determine when to acquire an image and manually trigger the CT scanner to acquire the image. As such, the interventionalist may error on the conservative side and initiate scanning before necessary, which may increase patient dose relative to initiating scanning a little later in time, while mitigating initiating scanning later than desired. Furthermore, the interventionalist is tasked with acts outside of the interventional procedure (i.e., determining when to scan and initiating scanning), and time consumed performing these acts could otherwise be used to perform the interventional procedure and/or interact with the patient.

SUMMARY OF THE INVENTION

Aspects of the present application address the above-referenced matters and others.

According to one aspect, a system includes an interventional apparatus and an imaging scanner. The interventional apparatus includes an interventional instrument configured to perform an image-guided interventional procedure for a patient. The interventional apparatus includes a position detector that detects a position of the interventional instrument within a region of the patient at which the image-guided interventional procedure is performed from outside of the region of interest and generates a signal indicative of the detected position. The imaging scanner includes a controller that activates the imaging scanner to scan the region of interest and the interventional instrument therein for one or more data acquisition cycles based on the movement signal.

According to another aspect, a method includes generating, with a position detector of an interventional apparatus, a movement signal indicative of a distance an interventional instrument of the interventional apparatus moves within a region of interest of a patient during an image-guided interventional procedure. The method further includes conveying the movement signal from the interventional apparatus to an imaging scanner used to generate images for the image-guided interventional procedure. The method further includes controlling, with a controller of the imaging scanner, scanning by the imaging scanner of the region of interest and the interventional instrument therein based on the movement signal for the image-guided interventional procedure.

According to another aspect, a computing readable storage medium encoded with computer readable instructions, which, when executed by one or more processors of a computing system, cause an imaging scanner to automatically scan a region of interest of a patient and an interventional instrument, of an interventional apparatus, therein in response to the a signal generated by the interventional apparatus, which is indicative of a movement of the interventional instrument within the region of interest, satisfying a predetermined threshold.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION

Figure 1:
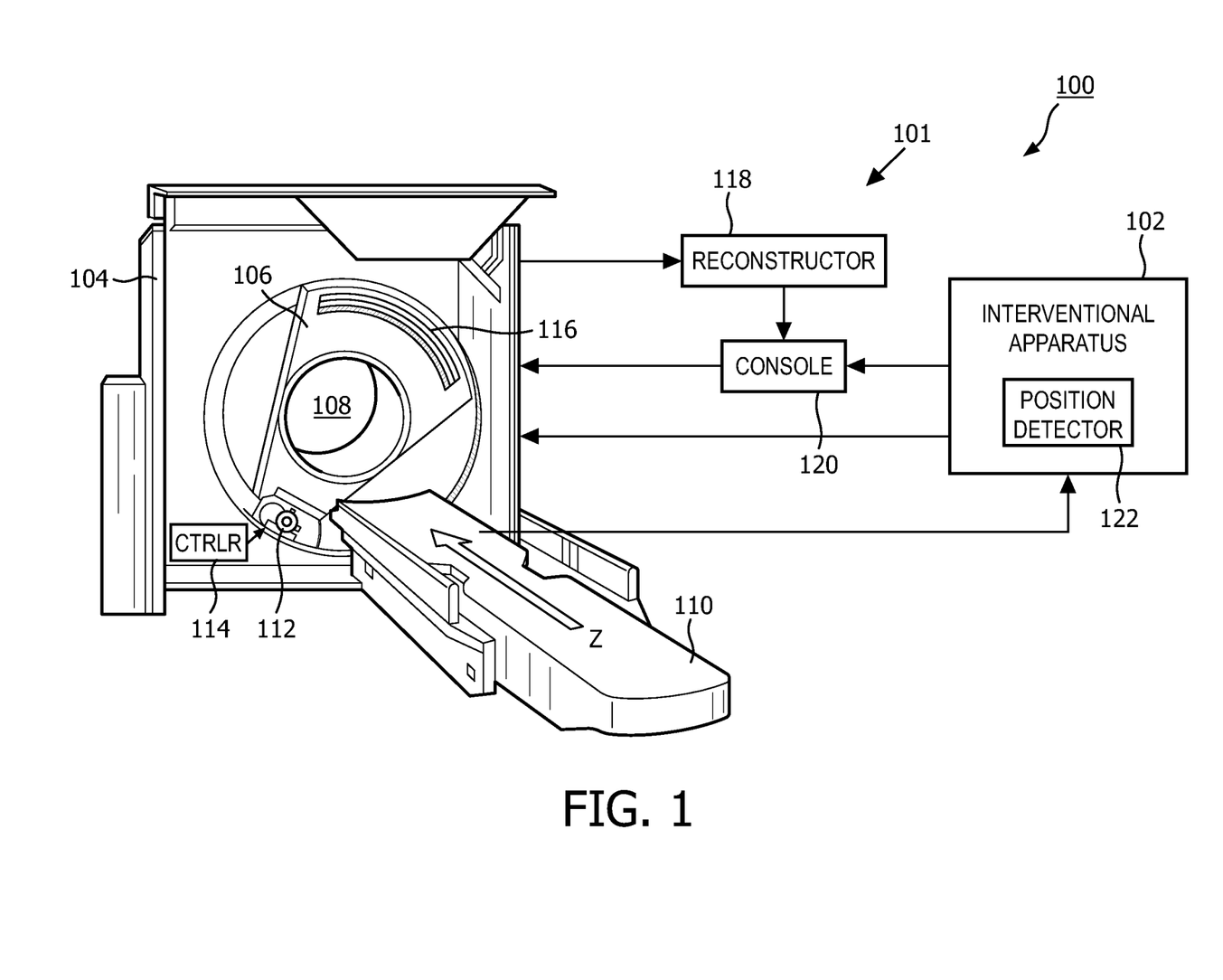
FIG. 1 schematically illustrates an example imaging system in connection with an interventional apparatus.

FIG. 1 illustrates a system 100 including an imaging scanner 101, such as a computed tomography (CT) imaging scanner, in connection with an interventional apparatus 102.

The illustrated imaging scanner 101 includes a stationary gantry 104 and a rotating gantry 106, which is rotatably supported by the stationary gantry 104. The rotating gantry 106 rotates around an examination region 108 about a longitudinal or z-axis. A patient support 110, such as a couch, supports a patient in the examination region 108 and is movable along the x, y and/or z-axis in coordination with the rotation of the rotating gantry 106.

A radiation source 112, such as an x-ray tube, is supported by and rotates with the rotating gantry 106 around the examination region 108. A controller ("CTRLR") 114 controls the radiation source 112. By way of non-limiting example, the illustrated controller 114 is configured to activate the radiation source 112 (i.e., turn the radiation source 112 "on" such that the radiation source 112 emits radiation that traverses the examination region 108) and deactivate the radiation source 112 (i.e., turn the radiation source 112 "off" such that such radiation does not traverses the examination region 108). A radiation sensitive detector array 116 detects radiation that traverses the examination region 108 and generates projection data indicative of the detected radiation.

A reconstructor 118 reconstructs the projection data and generates volumetric image data indicative of the examination region 108. The image data can be displayed, filmed, etc. A general purpose computing system serves as an operator console 120, and includes an output device such as a display and an input device such as a keyboard, mouse, and/or the like. The console 120 includes a processor(s) and computer readable storage medium (e.g., physical memory) encoded with computer readable instructions, which, when executed by the processor allows a user to operate the scanner 101 such as initiating scanning, display reconstructed images, etc. Additionally or alternatively, the processor can execute computer readable instructions carried in signal medium (e.g., a carrier wave).

As briefly discussed above, the illustrated imaging scanner 101 is shown in connection with the interventional apparatus 102. As described in greater detail below, the interventional apparatus 102 includes a position detector 122 that is configured to communicate with the imaging scanner 101, for example, to convey a signal to the imaging scanner 101 (e.g., the console 120 and/or the source controller 114) that triggers the imaging scanner 101 (e.g., with or without user interaction) to perform an action, such as activate the radiation source 112 and acquire data (i.e., perform a scan), based on a state such as a movement state or other state of the interventional apparatus 102 with respect to predetermined scan activation criteria, and/or other action.

As such, in one non-limiting embodiment, during an image-guided interventional procedure utilizing the interventional apparatus 102, the interventionalist does not have to determine when to scan a region of interest of the subject (and the interventional instrument therein) positioned in the examination region 108 or manually trigger the imaging scanner 101 to scan the region of interest. Instead, the position detector 122 senses information about the position state of the interventional procedures and this information is utilized to determine when to scan the portion of the subject in the examination region 108 and to automatically trigger the scanner 101 to scan the subject. The foregoing allows the interventionalist to focus on the procedure and the patient, and may facilitate reducing patient dose relative to a configuration in which the position detector 122 is omitted. Of course, the interventionalist can still manually initiate scanning via the imaging scanner 101 to scan the subject and/or pause or terminate an automatically triggered scan.

Figure 2:
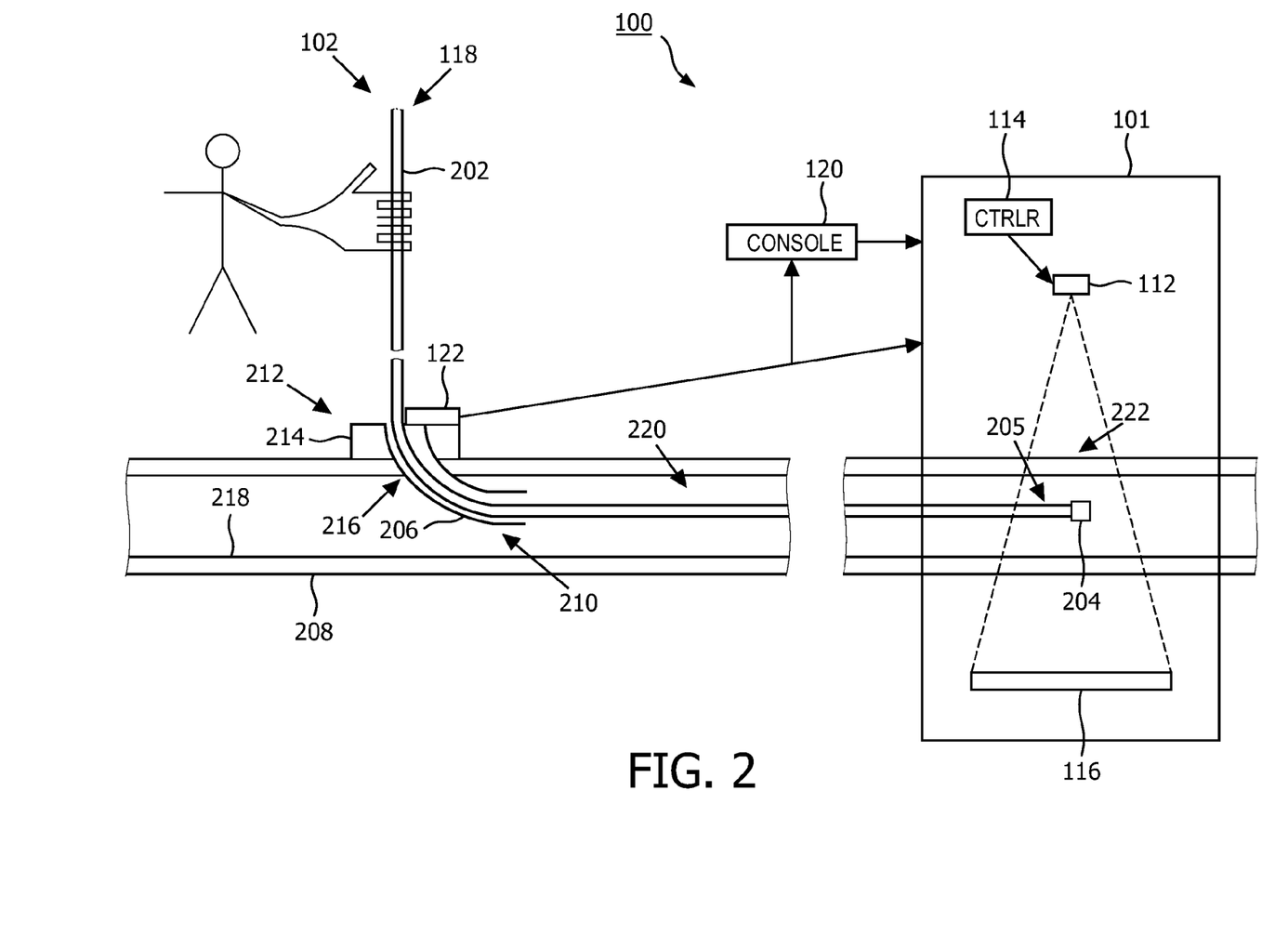
FIG. 2 illustrates an example of an interventional apparatus that includes a position detector that senses a position of a moveable portion of the interventional apparatus moveable during an image-guided procedure to facilitate performing the procedure.

FIG. 2 schematically illustrates an example of the interventional apparatus 102 in connection with an example image guided procedure.

In this example, the interventional apparatus 102 includes an elongate flexible catheter 202 with an interventional instrument 204 affixed to an end 205 of the catheter 202 that enters an object or subject 208 and a sheath 206 through which the catheter 202 enters the object or subject 208. The illustrated sheath 206 includes a first end 210, which is inserted into the object or subject 208, and a second end 212 which remains outside of the object or subject 208. The second end 212 includes a hub or port 214, which, generally, is geometrically larger than the first end 210 and sits or rests about an entry or access point 216 into the object or subject 208 created by the sheath 206.

The object or subject 208 includes a tubular structure 218 that provides a pathway 220 to a region of interest 222 of the object or subject 208. In the illustrated embodiment, the position detector 122 is disposed in connection with the hub 214 of the sheath 206 and can sense positional (e.g., translational, rotational, etc.) information about the catheter 202 relative to the sheath 206. For example, the illustrated position detector 122 senses movement of the catheter 202 in and out of the sheath 206, rotation of the catheter 202 within the sheath 206, etc., and generates a movement signal indicative of the sensed movement.

The position detector 122 may be variously affixed to the sheath 206. For example, in one embodiment, the position detector 122 may be part of the sheath 206. In another embodiment, the position detector 122 is separate from but fixidly attached to the sheath 206 via an adhesive such as glue. In yet another embodiment, the position detector 122 is removeably attached to the sheath 206. With this embodiment, a position detector 122 may be cleanable (e.g., sterilizeable, disinfectable, etc.) and alternately used with more than one sheath 206. The position detector 122 conveys the movement signal to the controller 114, directly and/or to the console 120, via a wireless or wired (e.g., a cable) communications channel.

At least one of the console 120 or the controller 114 executes computer readable instructions for evaluating the movement signal and determining whether to activate the imaging scanner 101 to scan. In the illustrated embodiment, the computer readable instructions compute a distance that the catheter 202 has traveled (e.g., from the beginning of the procedure, relative to a last scan, relative to an identified landmark within the object or subject, etc.) based on the movement signal and compares this distance with a stored predetermined threshold distance. In one instance, where the distance in the movement signal satisfies the threshold, the controller 114 transmits a command signal that activates the source 112 to scan for a predetermined number of data acquisition cycles. Optionally, the console 120 can provide a notification indicating that the source 112 will be activated within a predetermined time period before activating the source 112. Otherwise, the controller 114 does not activate the source 112 to scan.

In a variation of the above, the console 120 visually presents or provides a notification that indicates that data should be acquired and waits for a user confirmation. Such confirmation could be through an audible command such as a voice command from the user. Additionally or alternatively, the confirmation could be through a joystick, a foot pedal, a keyboard, a mouse, and/or other known input device. Additionally or alternatively, the user can manually invoke the imaging scanner 101 to acquire data independent of the trigger signal via an audible command and/or a joystick, a foot pedal, a keyboard, a mouse, the console 120, and/or other known input device.

In a non-limiting application of the above, the subject 208 is a human patient, the entry point 216 is the femoral artery via the groin, and thus the sheath 206 is partially inserted into the femoral artery at the groin, with a sub-portion of the sheath 206 including the hub 214 remaining outside of the patient at the groin. In this example, the region of interest 222 is anatomical structure such as the heart (or brain, lungs, etc.), and the interventional device 204 affixed to the end of the catheter 202 is configured for performing an interventional procedure at the structure of interest. Examples of cardiac interventional procedures include, but are not limited to, angioplasty, angiography, balloon septostomy, etc.

The position detector 122 senses movement of the catheter 202 within the region of interest 222 based on movement of the catheter 202 with respect to the position detector 122, and, if it is determined the movement of the catheter 202 corresponds to a distance that satisfies the predetermined distance threshold value, then the controller 114 invokes the scanner 101 to acquire data. The resulting displayed image visually shows the location of the interventional instrument 204 within the region of interest 222. The interventionalist performing the procedure can utilize the displayed image to facilitate guiding and employing the interventional instrument 204 in connection with the interventional procedure.

Figure 3:
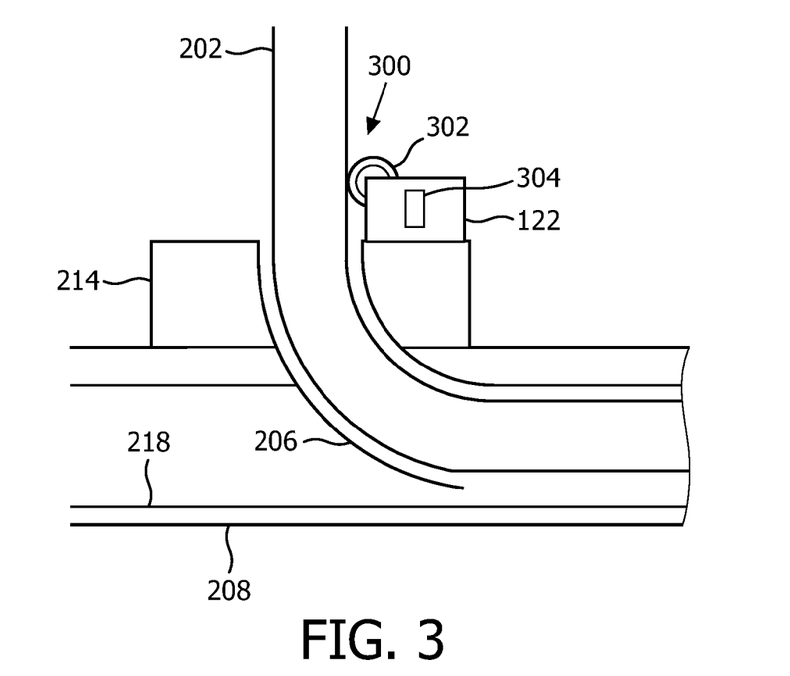
FIG. 3 illustrates an example of the position detector including a mechanical motion sensor.

FIG. 3 schematically illustrates a non-limiting embodiment of the position detector 122 including a mechanical based motion sensor.

In this embodiment, the position detector 122 includes at least one element 300 configured to rotate. For explanatory purposes, the at least one element 300 includes a wheel 302. However, other elements such as a ball, a roller, or other rotating element 300 may additionally or alternatively be used.

The illustrated wheel 302 is rotatably supported by the position detector 122, for example, via a pin, rod, or the like through a center axis of the wheel 302. Furthermore, the position detector 122 is affixed to the hub 214 such that the wheel 302 physically contacts an outer surface of the catheter 202 in response to the catheter 202 in the sheath 206. A mechanism such as a spring or the like may be used to exert a force that facilitates ensuring physical contact of the wheel 302 with the catheter 202.

A transducer 304, such as a rotary encoder or the like, senses the rotational position of the wheel 302 relative to a predetermined reference position. The transducer 304 generates an analog or digital signal indicative of the rotational position of the wheel 302 relative to the reference position. The position detector 122 conveys the signal to the console 120 and/or controller 114.

With this embodiment, each angular increment of the wheel 302 corresponds to a translational distance along the catheter 202. As such, the signal from the position detector 102 is indicative of a translational movement distance of the catheter 202 in the sheath 206 and hence in the region of interest of the subject 208. The wheel 302 is free to rotate in either direction, and the signal indicates the direction and magnitude of the movement, into or out of the sheath 206.

In the illustrated embodiment, the position detector 122 includes single wheel 302. In a variation, the position detector 122 may include more than one wheel 302 and/or other rotating element 300. With this variation, one or more of the wheels 302 and/or other rotating element 300 may be used to determine the rotational position.

Figure 4:
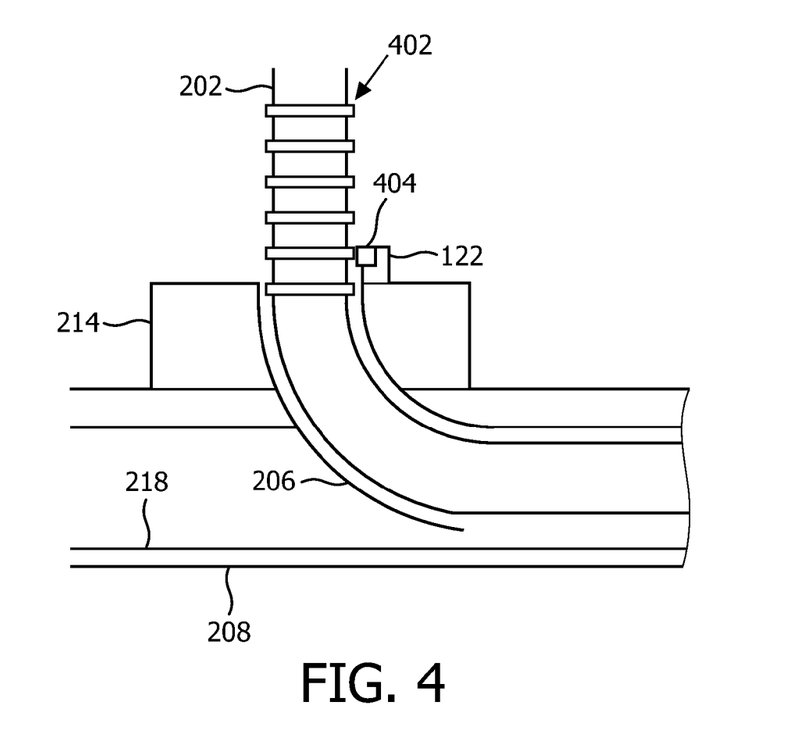
FIG. 4 illustrates another example of the position detector including a mechanical motion sensor.

FIG. 4 schematically illustrates another non-limiting embodiment of the position detector 122 including a mechanical based motion sensor.

In this embodiment, the catheter 202 includes a plurality of protrusions or nubs 402, protruding outward from the catheter 202. The plurality of protrusions 402 are separated from each other by a known distance, which correspond to a length of catheter 202 between protrusions 402. The protrusions 402 may be part of the catheter 202 (e.g., ribs) or affixed thereto. The position detector 122 includes a transducer 404 or the like which, in response to physically contacting one of the protrusions 402, generates a signal indicative of the physical contact.

The position detector 122 conveys the signal to the console 120 and/or controller 114. With this embodiment, since the plurality of protrusions 402 are spaced at known distances, each signal indicating a protrusion 402 has been detected corresponds to a translational distance of the catheter 202. As such, the signal from the position detector 122 is indicative of a translational movement distance of the catheter 202 in the sheath 206 and the region of interest of the object or subject 208. As with the wheel 302, the transducer 404 can indicate the direction and magnitude, and rotational or other motion of the catheter 202 in the sheath 206.

Figure 5:
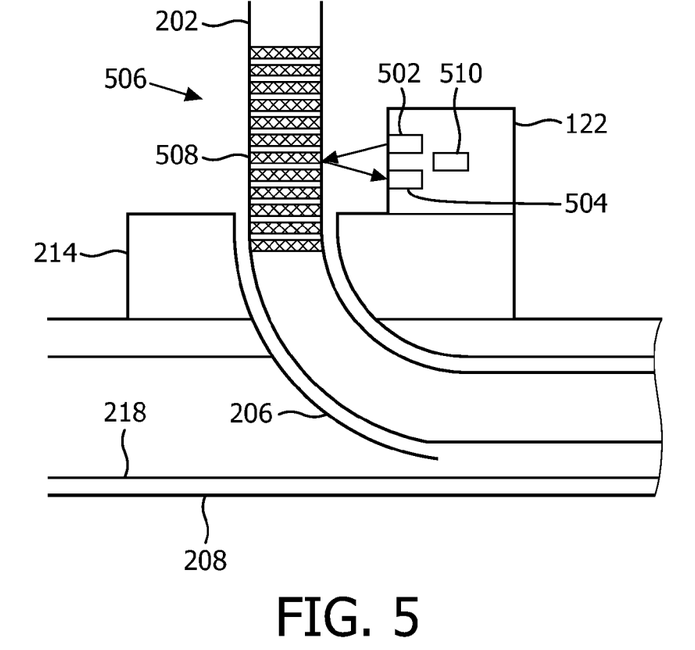
FIG. 5 illustrates an example of the position detector including an optical motion sensor.

FIG. 5 schematically illustrates another non-limiting embodiment of the position detector 122 including an optical based motion sensor.

In this embodiment, the position detector 122 includes a transmitter 502 and a receiver 504, and the catheter 202 includes a predetermined pattern 506 with a known reflective characteristic. By way of non-limiting example, the illustrated pattern 506 includes a plurality of bars 508 of alternating different colors (e.g., white and black, or red, green, blue, etc.) in which a distance between a given set of bars corresponds to a known translation distance. In other embodiment, the pattern 506 includes other reflective indicia. A power source 510 such as a battery provides power to energize the transmitter 502 and the receiver 504.

In operation, the transmitter 502 (e.g., a light emitting diode (LED) or other light source) transmits light which illuminates the catheter 202 and reflects off the pattern 506. The receiver 504 receives the reflected light and generates a signal indicative thereof. Since the bars 508 are spaced at known distances, the signal generated by the receiver 504 corresponds to a distance moved by the catheter 202. As such, the signal from the position detector 122 is indicative of a movement distance of the catheter 202 in the sheath 206 and hence in the region of interest of the object or subject 208.

In a variation, each bar 508 could also have a pattern, which can be used to determine rotational motion of the catheter 202. Similar to above, the pattern can be determined based on the detected reflected signal, and a rotational distance can be determined based on the detected reflected signal.

Figure 6:
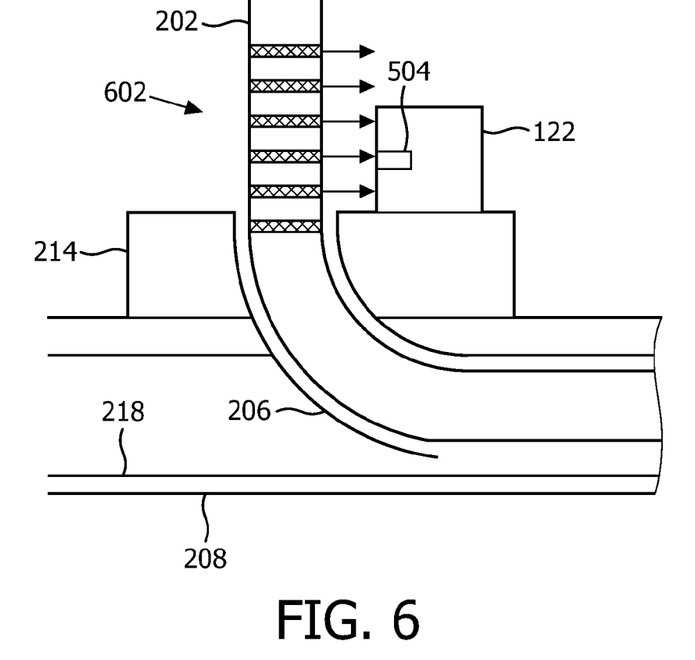
FIG. 6 illustrates another example of the position detector including an optical motion sensor.

FIG. 6 schematically illustrates a variation of FIG. 5 in which a plurality of light transmitters 602, powered by a battery or otherwise, are located along the catheter 202 at known distances apart and emit light that is detected by the receiver 504. Since the light transmitters 602 are spaced at known distances, the signal from the receiver 504 corresponds to a translational distance of the catheter 202. As such, the signal from the position detector 122 is indicative of a translational movement distance of the catheter 202 in the sheath 206 and hence in the region of interest of the object or subject 208.

Figure 7:
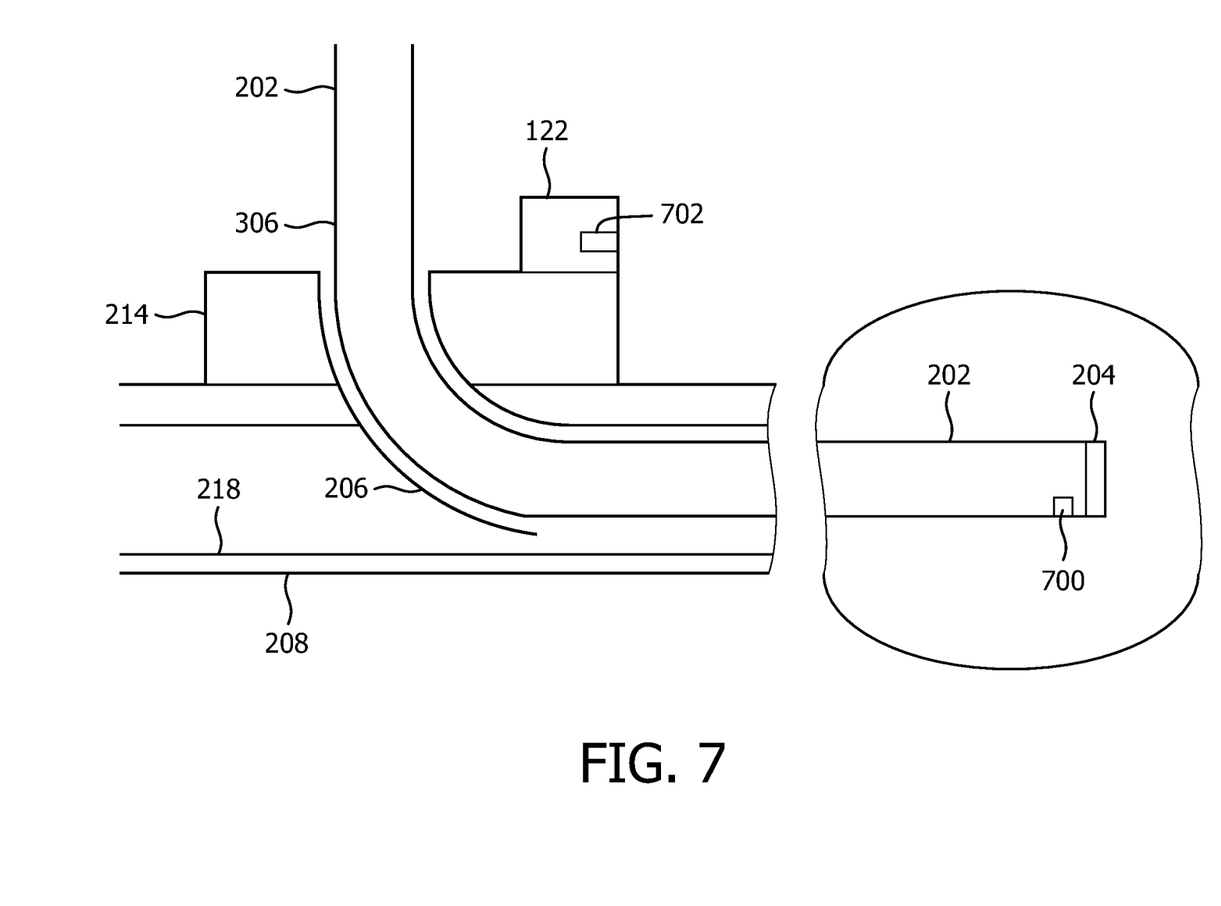
FIG. 7 illustrates an example of the position detector including a radio frequency motion sensor.

FIG. 7 schematically illustrates another non-limiting embodiment of the position detector 122 including a radio frequency based motion sensor.

In this embodiment, a passive emitter 700 is attached to (e.g., embedded in, affixed to, etc.) the catheter 202, near the interventional instrument 204, and the position detector 122 includes a transceiver 702 that transmits signals having a wavelength within a predetermined wavelength range. The passive emitter 700, in response to receiving signal in the predetermined wavelength range, emits a characteristic signal, which is received by the transceiver 702.

A signal strength of the received signal indicates a relative distance between the passive emitter 700 and the transceiver 702, and the transceiver 702 generates a signal indicative of the signal strength. Where the distance between the passive emitter 700 and the transceiver 702 corresponds to an length of the catheter 202 inserted into the sheath 206, the signal from transceiver 702 is indicative of the translational movement of the catheter 202.

It is to be understood that the examples of FIGS. 3-7 are non-limiting and other approaches are contemplated herein. In addition, one or more of the approaches of FIGS. 3-7 and/or other approaches can be combined, modified, etc.

Figure 8:
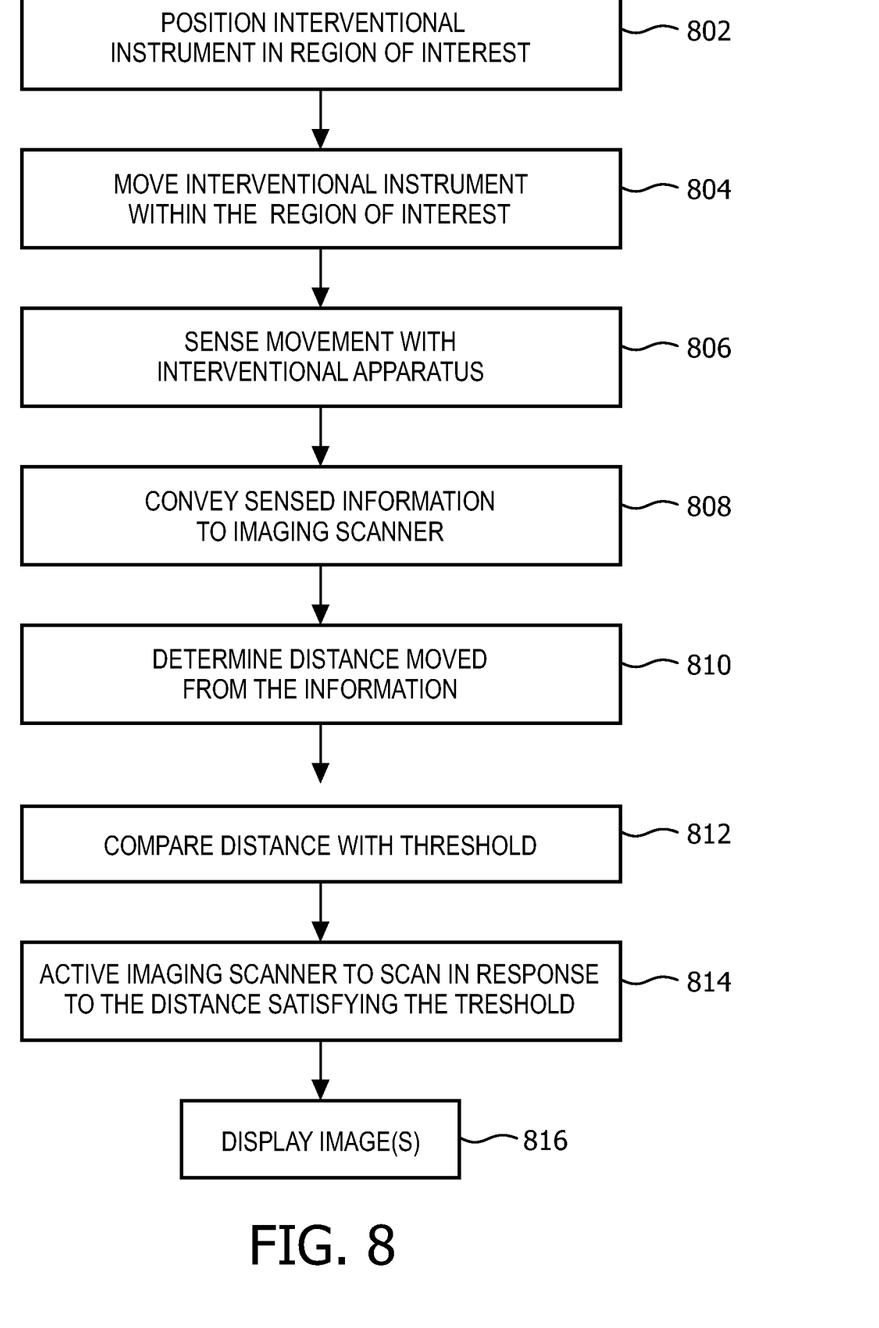
FIG. 8 illustrates example method for activating scanning with the interventional apparatus during an image-guided interventional procedure performed using the interventional apparatus.

FIG. 8 illustrates a method for activating scanning by an imaging scanner during an image-guided interventional procedure by the interventional apparatus.

It is to be appreciated that the ordering of the following acts is non-limiting. As such, other orderings are also contemplated herein. Furthermore, one or more of the following acts may be omitted and/or one or more acts may be added.

At 802, an interventional instrument of an interventional apparatus is positioned within a region of interest within a patient as described herein.

At 804, the interventional instrument is moved within the region of interest, for example, by an interventionalist performing the interventional procedure with the interventional apparatus.

At 806, a sensor of the interventional apparatus senses the movement and generates a signal indicative thereof.

At 808, the signal is conveyed to the imaging scanner.

At 810, the signal is evaluated to determine a relative distance the interventional instrument has moved within the patient.

At 812, the distance is compared with a predetermined scanning threshold distance.

At 814, the scanner is activated to scan only in response to the distance satisfying the threshold. As such, scans are performed automatically only when needed.

At 816, one or more images generated from the scan are displayed.

Otherwise and/or afterwards, acts 804-814 are repeated one or more times.

Although described above in connection with computed tomography (CT), it is to be appreciated that the above is also applicable to other imaging modalities such as, but not only, positron emission tomography (PET), single photon emission tomography (SPECT), magnetic resonance imaging (MRI), ultrasound (US), three dimensional (3D) x-ray, and/or other imaging modalities.

The invention has been described herein with reference to the various embodiments. Modifications and alterations may occur to others upon reading the description herein. It is intended that the invention be construed as including all such modifications and alterations insofar as they come within the scope of the appended claims or the equivalents thereof.

What is claimed is:

1. A system, comprising:
    an imaging scanner configured with an examination region and to scan the examination region;
    an interventional apparatus including an interventional instrument affixed to a catheter, and configured for an image-guided interventional procedure of a patient with a region of interest positioned in the examination region of the imaging scanner, the interventional apparatus including a position detector configured for location outside the examination region that detects changes in position of the interventional instrument moving within the examination region based on movement of the catheter and generates a movement signal indicative of the detected changed position; and
    wherein the imaging scanner includes a controller that activates the imaging scanner based on the movement signal from the interventional apparatus to scan the examination region for one or more data acquisition cycles.

2. The system of claim 1, wherein the interventional apparatus comprises:
    a sheath that is tubular with openings at each end and configured to provide an entry point into a tubular vessel of the patient;
    wherein the catheter is configured to be fed through the sheath; and
    wherein the position detector, affixed to one end of the sheath, detects movement of the catheter relative to the sheath indicative of the detected changed position of the interventional instrument and generates the movement signal according to the movement of the catheter.

3. The system of claim 2, wherein the movement signal indicates a distance that the catheter has traveled, and the controller activates the imaging scanner to scan the examination region in response to the distance satisfying a predetermined distance threshold.

4. The system of claim 1, wherein the controller automatically activates the imaging scanner to scan the examination region and reconstruct an image from the scan without user interaction.

5. The system of claim 1, wherein the position detector includes a mechanical based motion sensor that senses the movement of the catheter relative to the sheath.

6. The system of claim 1, wherein the position detector comprises:
    at least one element configured for physical contact with the catheter and to rotate in coordination with the movement of the catheter through the sheath; and
    a transducer that senses rotation movement of the at least one element and generates the movement signal indicative of the sensed rotation.

7. The apparatus of claim 6, wherein a distance, of the rotational movement of the at least one element corresponds to a translational distance of the catheter.

8. The system of claim 2,
    wherein the catheter comprises a plurality of protrusions spaced apart along a long axis of the catheter at predetermined distances from each other; and
    wherein the position detector comprises a transducer configured to detect each protrusion of the plurality of protrusions passing the transducer and to generate the movement signal indicative of the passing protrusions.

9. The system of claim 1, wherein the position detector includes an optical based motion sensor that senses the movement of the catheter.

10. The system of claim 9, wherein the catheter includes a pattern thereon that is responsive to light, and the optical motion sensor comprising:
- a transmitter that transmits first light that illuminates the pattern on the catheter; and
- a receiver that receives second light reflected off the pattern and generates the movement signal, which is indicative of the detected second light.

11. The apparatus of claim 10, wherein changes in the pattern indicates a movement distance of the catheter.

12. The system of claim 1, wherein the position detector includes a radio frequency based motion sensor that senses the movement of the catheter.

13. The system of claim 12, wherein the catheter comprises an emitter configured to respond to reception of a signal having a predetermined wavelength, wherein, upon receiving the signal having the predetermined wavelength, the emitter emits a signal; and
- wherein the position detector comprises a transceiver that transmits the signal based on a predetermined periodicity and receives the emitted signal, and generates the movement signal, which is indicative of a changed signal strength of the received emitted signal.

14. The apparatus of claim 13, wherein the signal strength of the emitted signal is indicative of a distance between the emitter and the transceiver and a change in the signal strength indicates a movement distance of the catheter.

15. A method, comprising:
- generating, with a position detector of an interventional apparatus, a movement signal indicative of a distance an interventional instrument affixed to a catheter of the interventional apparatus moves within an examination region of an imaging scanner during an image-guided interventional procedure within a region of interest of a patient based on movement, of the catheter, wherein the position detector detects the moved distance of the interventional instrument from outside the examination region of the imaging scanner;
- conveying the movement signal from the interventional apparatus to the imaging scanner used to generate images for the image-guided interventional procedure; and
- controlling, with a controller of the imaging scanner, scanning by the imaging scanner of the examination region activated by the movement signal according to the interventional apparatus exceeding a predetermined threshold with the region of interest and the interventional instrument both positioned in the examination region.

16. The method of claim 15, wherein the interventional apparatus comprises a sheath that is tubular with openings at each end and configured to provide an entry point into a tubular vessel of the patient;
- wherein the catheter is configured to be fed through the sheath; and
- wherein the position detector, affixed to one end of the sheath, detects movement of the catheter relative to the sheath and generates the movement signal based thereon.

17. The method of claim 15, further comprising:
- comparing the movement signal with a predetermined scanner activation threshold value; and
- activating the image scanner to scan the examination region with both the positioned region of interest and the interventional instrument therein only in response to the movement signal satisfying the predetermined scanner activation threshold value.

18. The method of claim 17, wherein the image scanner is automatically activated according to the movement signal without human interaction.

19. The method of claim 15, further comprising:
- displaying one or more images generated by the imaging scanner in response to scanning the examination region with both the region of interest and the interventional instrument therein.

20. A non-transitory computing readable storage medium encoded with computer readable instructions, which, when executed by one or more processors of a computing system, cause an imaging scanner to automatically scan an examination region of the imaging scanner with both a region of interest of a patient and an interventional instrument affixed to a catheter positioned therein, in response to a signal generated by a position detector that detects movement of a portion of the catheter located outside of the examination region satisfying a predetermined threshold, which is indicative of a movement of the interventional instrument within the region of interest.

* * * * *